:::

United States Patent
Brown et al.

(10) Patent No.: US 6,601,016 B1
(45) Date of Patent: Jul. 29, 2003

(54) MONITORING FITNESS ACTIVITY ACROSS DIVERSE EXERCISE MACHINES UTILIZING A UNIVERSALLY ACCESSIBLE SERVER SYSTEM

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/561,426

(22) Filed: Apr. 28, 2000

(51) Int. Cl.[7] ............................................... G06F 15/00
(52) U.S. Cl. ....................................................... 702/182
(58) Field of Search .......................... 272/93, 118, 134; 482/9, 7, 57, 8, 5, 92; 221/211; 364/900, 942; 116/55; 343/357

(56) References Cited

U.S. PATENT DOCUMENTS

| | | | | |
|---|---|---|---|---|
| 4,817,940 A | * | 4/1989 | Shaw et al. ..................... | 272/93 |
| 4,828,257 A | | 5/1989 | Dyer et al. | |
| 4,891,785 A | * | 1/1990 | Donohoo ..................... | 364/900 |
| 5,204,670 A | | 4/1993 | Stinton | |
| 5,213,555 A | * | 5/1993 | Hood et al. ..................... | 482/57 |
| 5,335,188 A | | 8/1994 | Brisson | |
| 5,387,164 A | * | 2/1995 | Brown, Jr. ..................... | 482/9 |
| 5,435,799 A | * | 7/1995 | Lundin ........................... | 482/8 |
| 5,598,849 A | | 2/1997 | Browne | |
| 5,702,323 A | | 12/1997 | Poulton | |
| 5,785,632 A | * | 7/1998 | Greenberg et al. ............. | 482/5 |
| 5,799,281 A | | 8/1998 | Login et al. | |
| 5,816,443 A | * | 10/1998 | Bustos ........................ | 221/211 |
| 5,888,172 A | * | 3/1999 | Andrus et al. ................. | 482/7 |
| 5,937,387 A | | 8/1999 | Summerell et al. | |
| 5,957,699 A | | 9/1999 | Peterson et al. | |
| 5,973,696 A | * | 10/1999 | Agranat et al. ............. | 345/357 |
| 5,976,083 A | | 11/1999 | Richardson et al. | |
| 5,984,839 A | | 11/1999 | Corkum | |
| 6,042,519 A | * | 3/2000 | Shea ........................... | 482/57 |
| 6,464,618 B1 | | 10/2002 | Shea | |

OTHER PUBLICATIONS

Concept II, Inc. What is the Concept II Indoor Rower?.

* cited by examiner

*Primary Examiner*—John Barlow
*Assistant Examiner*—Tung Lau
(74) *Attorney, Agent, or Firm*—Marilyn Smith Dawkins; Bracewell & Patterson, L.L.P.

(57) ABSTRACT

According to the present invention, current fitness indicators for a particular user are detected by a particular exercise machine monitoring device that monitors exercise performed by the particular user on a particular exercise machine. The current fitness indicators are transmitted in a particular transmittable data format to a universally accessible server system in accordance with a universal identifier associated with the particular user and stored at said universally accessible server system in accordance with the universal identifier as current fitness activity, such that real-time fitness activity for a user computed from fitness activity received from any of multiple diverse exercise machines over a period of time is monitored by a universally accessible server system according to a universal identifier for a particular user.

60 Claims, 6 Drawing Sheets

MONITORING FITNESS ACTIVITY ACROSS DIVERSE EXERCISE MACHINES UTILIZING A UNIVERSALLY ACCESSIBLE SERVER SYSTEM

CROSS-REFERENCE TO RELATED APPLICATIONS

The present application is related to the following co-pending applications, which are filed on even date herewith and incorporated herein by reference:

(1) U.S. patent application Ser. No. 09/561,115;
(2) U.S. patent application Ser. No. 09/561,134;
(3) U.S. patent application Ser. No. 09/561,422; and
(4) U.S. patent application Ser. No. 09/561,130.

BACKGROUND OF THE INVENTION

1. Technical Field

The present invention relates to an improved method, system and program for monitoring fitness activity in general and, in particular, to an improved method, system and program for monitoring fitness activity across diverse exercise machines utilizing a universally accessible server system. Still more particularly, the present invention relates to a method, system and program for monitoring the real-time cumulative fitness activity of a user from fitness activity data received from a plurality of diverse exercise machines over a period of time utilizing a universally accessible server system according to a universal identifier associated with the user.

2. Description of the Prior Art

A fitness craze has recently swept the United States and other countries. From fat-free potato chips to treadmills, people around the world have become obsessed with weight loss and healthy living. Accordingly, record numbers of new fitness products/exercise equipment from multiple manufacturers have emerged to meet this obsession (including stair climbers, treadmills, recumbent bicycles, ski machines, rowing machines, and the like).

Many pieces of exercise equipment, when utilized regularly, are very useful for weight loss, for improving cardiovascular stamina, and for strengthening various muscles. Most exercise equipment includes a monitoring device that may include a pulse monitor, a distance meter, a rate monitor, a time monitor, a strain gauge, an accelerometer and/or any other sensor for measuring the physical activity/performance level of an user on the equipment. Moreover, monitoring devices typically request personal data from the user such as age, weight and desired physical fitness level. The monitoring device utilizes the personal data in combination with physical exertion and heart rate to estimate calories burned, fitness levels met, and other fitness related data. In addition, the monitor may adjust the resistance or speed of a piece of exercise equipment in order to aid the user in reaching and/or maintaining a fitness level for that exercise session.

One limiting factor of many exercise machines and monitors is that the user must reenter their personal data to the monitor each time the user utilizes an exercise machine. In addition, most exercise machines do not have a previous history of the user from which to provide data about improvement and to provide additional fitness goals. However, one solution to providing a history of users is provided in U.S. Pat. No. 5,335,188 ('188). In '188, a speed and time elapsed in an exercise session on a bicycle is recorded. The user may choose to save the speed and time of an exercise session under an identifier for the user. The user may later select a particular exercise session as a standard of performance for subsequent performances whereby each subsequent performance is compared with the selected exercise session. However, while the bicycle monitor memory stores exercise sessions for a particular user at that bicycle, in a club or other venue where multiple bicycles are provided, the user may not always have access to the bicycle at which the session data is stored.

Another limiting factor of many exercise machines is that they operate and monitor the user independent of one another. However, cross-training across multiple machines is popular in order to exercise different parts of the body. An individual may spend 20 minutes on a treadmill working a hills program where the monitor for the treadmill calculates a certain number of calories burned and other fitness related data. The individual may then move to a rowing machine that does not realize that the user has already worked for 20 minutes and thus calculates calories burned and other fitness related data as if the user only worked out on the rowing machine. An overall fitness level achieved by the user after working on both machines is not provided.

One solution to cross-training across multiple machines is provided in U.S. Pat. No. 5,598,849 ('849). In '849, an individual is provided with a user monitor that has a preferred exercise regimen of physical parameters such as heart rate stored therein. The user is required to monitor at least one physical parameter with the assistance of the user monitor and is preferably required during exercise to control his exercise to maintain the physical parameter as closely as possible to the preset values. After exercising is completed, the monitored physical parameters are proffered from the user monitor and sent to a master data processing system where the monitored parameters are stored and compared with the preset parameters in order to develop a fitness profile. However, a real-time fitness profile is not provided. In addition, the exercise regimen is not alterable during the workout. Moreover, the user monitor is limited in that operates independent of the exercise machine and therefore does not provide feedback to the exercise machine in order that resistance or another variable may be adjusted.

In addition, another limiting factor of many exercise machines is that they are boring to utilize because of their inability to encourage an user to continue exercising. Display screens that depict an user's location within a selected exercise program may be provided, however typically include dull graphics. One solution to improving graphical rendering is provided in U.S. Pat. No. 5,947,868 ('868). In the '868 patent, an exercise monitor outputs a signal representative of the performance level of an user utilizing the exercise equipment (e.g. pulse rate, distance traveled, time exercised, rate of exercise, etc.). The performance level signal then is fed to a video game player wirelessly or via a cable.

The video game player preferably includes a hand-held video game player. To simulate the user, the output from the exercise monitor is utilized to control the video game character's performance level within a video game that runs on the video game player. For example, the lifetime of a video game character may be increased by peddling faster. However, while the video game player provides a graphical venue by which the user controls a video game character according to their fitness level, other types of graphical rendering, other than a video game are not provided. In addition, in order to utilize the video game player, a monitor that supplies a particular type of performance level signal must be coupled to the exercise machine.

Another limiting factor of many exercise machines is that they do not provide a display that is adjustable dependent upon the user. For example, it would be preferable to provide for displaying output from an exercise machine in a particular language, dependent upon the user. In another example, it would be preferable to provide for displaying output from an exercise machine in a particular color or size of type. Moreover, display monitors may be provided that include a hyper-braille representation of text and fitness levels.

Therefore, in view of the aforementioned, it would be preferable to provide a personal electronic exercise monitor via a universally accessible server system according to a universal identifier that provides personal data and exercise program selections to an exercise machine monitor, operates in real-time to proffer fitness data from exercise machine monitors when utilized by a particular user, utilizes the fitness data from each exercise machine monitor to update a total fitness profile for a particular user, and designates the type of graphical rendering of current exertion and totals that is selected by the particular user. In addition, it would be preferable to provide a personal electronic exercise monitor utilizing a universally accessible server system from which personal data and/or exercise program selections are transmittable to an exercise machine monitor such that it is not necessary for a user to re-enter the data at multiple diverse exercise machines.

SUMMARY OF THE INVENTION

In view of the foregoing, it is therefore an object of the present invention to provide an improved method, system and program for monitoring fitness activity.

It is another object of the present invention to provide an improved method, system and program for monitoring fitness activity across diverse exercise machines utilizing a universally accessible server system.

It is yet another object of the present invention to provide an improved method, system and program for monitoring the real-time cumulative fitness activity of a user from fitness activity data received from a plurality of diverse exercise machines over a period of time utilizing a universally accessible server system according to a universal identifier associated with the user.

According to the method, system and program of the present invention, current fitness indicators for a particular user are detected by a particular exercise machine monitoring device that monitors exercise performed by the particular user on a particular exercise machine. The current fitness indicators are transmitted in a particular transmittable data format to a universally accessible server system in accordance with a universal identifier associated with the particular user and stored at said universally accessible server system in accordance with the universal identifier as current fitness activity, such that real-time fitness activity for a user computed from fitness activity received from any of multiple diverse exercise machines over a period of time is monitored by a universally accessible server system according to a universal identifier for a particular user.

All objects, features, and advantages of the present invention will become apparent in the following detailed written description.

DESCRIPTION OF THE DRAWINGS

The invention itself as will as a preferred mode of use, further objects, and advantages thereof, will best be understood by reference to the following detailed description of an illustrative embodiment when read in conjunction with the accompanying drawings, wherein.

DESCRIPTION OF A PREFERRED EMBODIMENT

The present invention may be executed in a variety of systems, including a variety of computers under a number of different operating systems. In a preferred embodiment of the present invention, a system of network servers, such as Netfinity™ servers (Netfinity™ is a trademark of International Business Machines Corp.) and other data processing systems connected to a network are utilized to house a universally accessible database. A computer system has access to the network servers. The computer system may be, for example, a desktop computer, a network computer, a portable computer, a midrange computer or a mainframe computer. In addition, the computer system may be part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
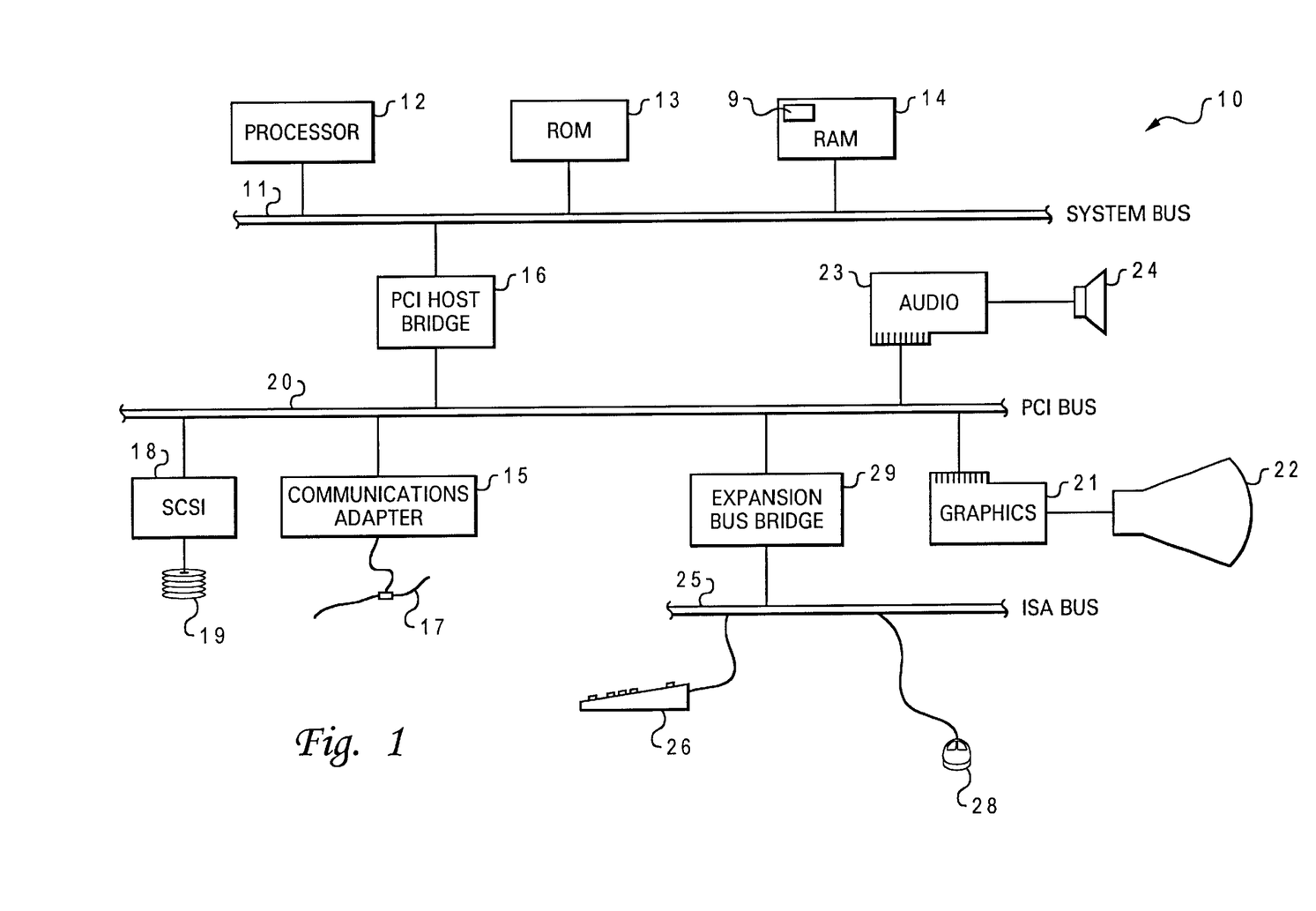
FIG. 1 depicts a block diagram of a typical computer system that may utilize a preferred embodiment of the present invention.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 4, 5, 6 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
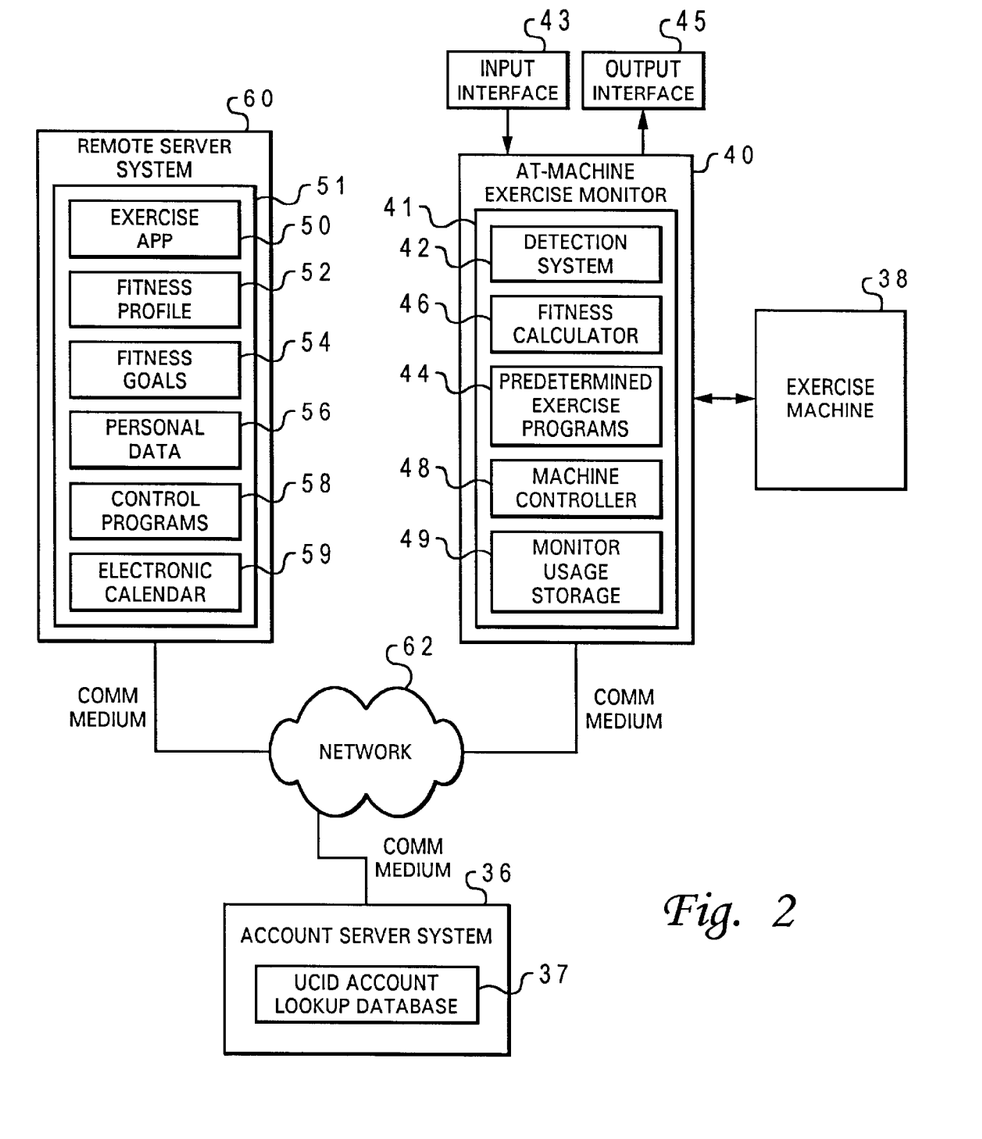
FIG. 2 illustrates a system for utilizing universally accessible server system as a personal electronic exercise monitor in accordance with the method, system and program of a preferred embodiment of the present invention.

With references now to FIG. 2, there is depicted a system for utilizing a universally accessible server system as a personal electronic exercise monitor in accordance with the method, system and program of a preferred embodiment of the present invention. As depicted, an at-machine exercise machine monitor 40 for an exercise machine 38 includes a detection system 42. Preferably, detection system 42 includes real-time monitoring systems such as a pulse monitor, a distance meter, a rate monitor, a time monitor, a strain gauge, an accelerometer and/or any other sensor for measuring the fitness indicators of physical activity/performance level of an user on a piece of equipment, as is well known in the art.

In addition, machine monitor 40 includes predetermined exercise programs 44, a fitness calculator 46 and a machine controller 48. Machine controller 48 transmits signals that control the moving parts of exercise machine 38. A user can select from predetermined exercise programs 44 that control machine controller 48 or a control program from a remote server system 60 according to a universal communications identifier (UCID) as will be further described. Predetermined exercise programs 44 preferably enables exercise machine 38 to simulate particular terrain such as hills or to regulate achieving a fitness goal such as improving cardiovascular strength. In addition, a user can select a particular level of difficulty for a selected exercise program for predetermined exercise programs 44. Fitness calculator 46 utilizes monitored data collected by detection system 42 and data about the user (e.g. age, weight) to estimate the number of calories burned and other fitness related statistics.

Predetermined exercise programs 44 are preferably stored in a data storage structure within data storage medium 41. In addition, fitness calculator 46 is preferably stored within data storage medium 41. While in the present embodiment data storage medium 41 is accessible locally by machine monitor 40, in alternate embodiments, data storage medium 41 may be remotely or externally accessible. In addition, machine monitor 40 may be a "dumb" terminal that is controlled by a network computer.

Moreover, machine monitor 40 preferably communicates with an input interface 43 and an output interface 45. Input interface 43 may include, but is not limited to including, a keyboard, a mouse, a stylus, a vocal recognition system, a tactile-detectable device, a biometric detection device, a disk drive, and other devices which allow user input to machine monitor 40. Preferably, input interface 43 provides an interface with machine monitor 40 through which a user may supplement data provided by machine monitor 40 and remote server system 60. In addition, input interface 43 preferably provides an interface with machine monitor 40 through which a user may customize the functions performed by machine monitor 40 and data stored therein.

In accordance with the present invention, machine monitor 40, remote server system 60, and account server system 36 communicate via a communications medium through a network 62. The communications medium may utilize wired or wireless communications or other communications media that enables transmission of data. Network 62 advantageously comprises a global network such as the Internet, however may also compares a local area network (LAN).

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies, such as secure socket layer (SSL) or virtual private networks (VPN).

An example of an XML data file for a control program that might be transmitted from remote server system 60 to machine monitor 40, as depicted below, preferably contains data that is distinguished by attributes on elements and may be wrapped within a larger element. For example, the data attributed to element "<TimeStamp> </TimeStamp>" designates the time that the data was attributed to the XML data file.

<TREADMILL TimeStamp="888965153" MachineType="Arc2000" UserID="JANEXYZ" Speed="30" Elevation="5">

In addition, in an alternate example, the XML data file might be formatted utilizing elements, as illustrated below.

<TimeStamp>888965153</TimeStamp>
    <MachineType>Arc2000</MachineType>
    <UserID>JANEXYZ</UserID>
    <Speed>30</Speed>
    <Elevation>5</Elevation>

In the example, as will be further described, machine monitor 40 would receive the example XML data file and utilize the XML data file to control an exercise program operating on exercise machine 38. The above described XML data file example is intended as a functional example of an XML data file that would control the speed and elevation of a treadmill. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for transmittal to a particular exercise machine is included in the XML data file. For example, a speed and elevation may be required to validate the XML data file.

Account server system 36 advantageously includes a universal communications identifier (UCID) lookup database 37 that includes a directory for accessing multiple UCID accounts. Advantageously, the listings for multiple UCID accounts that are stored in UCID lookup database 37 each match with a server address where the data for each UCID account is accessible and may include other data about the UCID account, such as the owner of the account, passwords for access to the account, etc. Account server 36 may include a single server system or multiple server systems that provide universal access to the listings of UCID accounts. In addition, multiple interfaces may be utilized for entering a UCID or multiple UCIDs in order to lookup and access a UCID account in lookup database 37. For example, a user may input a UCID or multiple UCIDs at input interface 43 of machine monitor 40.

The universally accessible database of server systems may include multiple remote servers, such as remote server system 60 that each access multiple data storage mediums, such as data storage medium 51. Remote servers may also include home computer systems, data storage provider server, web applications servers (WAPs), portable computers, and mainframes. In general, the data processing systems which include the universally accessible servers system preferably provide processing power for remotely executing applications and functions according to a UCID account. In addition, data stored according to a UCID account may be repurposed at an alternate server system that formats and converts the data into the common transmittable data format in transmittal from the universally accessible servers system to machine monitor 40. Moreover, the data stored according to a UCID account is advantageously accessible to machine monitor 40 via a live network connection, however may also be replicated locally on in a temporary storage medium 41 of machine monitor 40.

As will be further described, a UCID account includes an alphanumeric identifier associated with a particular server address that may be owned by an individual, group of individuals, a business, a government, etc. The alphanumeric identifier may be utilized to access multiple types of data formats and organizations of data including, but not limited to, web pages, databases, and data files. Alphanumeric identifiers may include listings including, but not limited to, web page identifiers, server identifiers, etc.

In addition, a single UCID account may utilize multiple alphanumeric identifiers for accessing multiple levels of an account. For example, a business UCID account may include an identifier, such as a web page address, that when requested allows any user to access the web page that provides a listing of available exercise machines provided by a particular health club. In addition, the business UCID account may include another web page address, that also requires a login name and password, to provide restricted access to a database of current exercisers. For example, a user may enroll in a stairclimber club where exercisers compete to see who can climb the most stairs. Each member of the club would be able to access the database of current exercisers and current stair counts via a particular web page by entering a valid login name and password. In another example, an individual may provide access to others to the individual's current cumulative fitness activity by a particular identifier such that a group of buddies can access the current cumulative fitness activity of each other and compete against one another. In addition, the location that the buddy is exercising may be attained.

Multiple types of data may be associated with each UCID account accessible via account lookup server system 36. In the present example, a UCID account includes the data stored in data storage medium 51. By entering the UCID for the UCID account at machine monitor 40, machine monitor 40 transmits the UCID to account lookup server system 36 that then points to remote server system 60 in order to establish a connection between remote server system 60 and machine monitor 40. Remote server system 60 may further include a directory of data stored in a data storage medium 51 according to multiple UCIDs.

In the present example, data storage medium 51 includes an exercise application 50, a fitness profile 52, fitness goals 54, personal data 56, control programs 58, and an electronic calendar 59. In particular, is exercise application 50, fitness profile 52, fitness goals 54, and personal data 56, control programs 58, electronic calendar 59 and other transmittable data stored data storage medium 51 according to a particular UCID account is preferably efficiently stored in a particular transmittable data format, such as XML.

Remote server system 60 is preferably enabled to execute an exercise application 50 to compute current fitness activity based on the detected exercise signals received from machine monitor 40 in the form of a pulse, distance, rate, time, strain, acceleration, and any other sensed value that may be utilized to compute current fitness activity. In addition, in calculating current fitness activity, factors such as previously accumulated fitness activity stored in fitness profile 52, personal data 56, and the type of exercise machine are utilized to compute a realistic fitness assessment.

In particular, in addition to receiving detected exercise signals from machine monitor 40, detected exercise may be input by a user via input interface 43 or from another monitoring device. For example, a user may count the number of jumping jacks that they perform during a break between utilizing exercise machines. The number of jumping jacks can be entered into machine monitor 40 via an input interface 43 and transmitted to remote server system 60. Remote server system 60 computes fitness activity data for the jumping jacks and updates the cumulative real-time fitness activity data.

Cumulative fitness activity over a selected time period is preferably computed by exercise application 50 from summing previously accumulated fitness activity for the selected time period with the current fitness activity. In summing the previously accumulated fitness activity and current fitness activity, remote server system 60 may adjust the cumulative total to more closely reflect the fitness gained as a result of exercising on multiple machines over a period of time. For example, if a user exercises for an hour across three different exercise machines, the amount of calories burned by the user actually increases with prolonged exercise over a particular amount of time determined for that user and therefore is adjusted in the cumulative fitness activity. Therefore, remote server system 60 is enabled to compute and store cumulative real-time fitness activity within fitness profile 52 over a selected time period or session from across multiple diverse exercise machines utilizing exercise application 50.

In addition to storing cumulative real-time fitness activity for a user over a particular period of time, individual sessions of fitness activity may also be recorded. For example, if a user exercises on a treadmill for 20 minutes and a rowing machine for 20 minutes, a cumulative fitness profile may be calculated and stored in fitness profile 52. In addition, fitness activity achieved from exercise on the treadmill and rowing machine may be stored as separate exercise sessions. Moreover, in addition to calculating cumulative fitness activity according to previously accumulated fitness activity, personal data 56 and the type of exercise machine, the types of food eaten by the user that day, fluid intake, medication usage and environmental exposure may be utilized to determine cumulative fitness activity data.

Fitness profile 52, fitness goals 54 and personal data 56 may be retrieved at machine monitor 40, wherein machine monitor 40 utilizes the data to calculate current cumulative fitness activity for a user. Current cumulative fitness activity calculated at machine monitor 40 is transmitted to remote server system 60 according to a UCID.

Personal data 56 stored on data storage medium 51 according to a UCID account may include information that is relevant to determining fitness gains in a workout such as weight, height, age, percentage body fat, bone density, metabolism, health problems, prescriptions, diet, and other health related factors. In addition, health data gathered for the user, such as food, liquid and medication intake and environmental exposure may be included. For example, food and liquid intake for a user may be monitored at a UCID account as described in U.S. patent application Ser. No. 09/466,051 and in U.S. patent application Ser. No. 09/560,386, herein incorporated by reference. In another example, medication intake for a user may be monitored at a UCID account as described in U.S. patent application Ser. No. 09/560,318, herein incorporated by reference. Moreover, environmental exposure of a user may be monitored at a UCID account as described in U.S. patent application Ser. No. 09/560,161, herein incorporated by reference.

In addition, personal data 56 preferably includes a user's output preference for how cumulative fitness activity should be output. For example, a user may prefer a particular font size, colors, output device, graphical application, etc.

Moreover, in personal data 56, an individual can designate multiple levels of security for accessing fitness profile 52, fitness goals 54 and personal data 56 stored on data storage medium 51. For example, particular parts of personal data 56 such as age and bone density may be shielded from transmittal and access without a password. As will be understood by one with ordinary skill in the art, multiple types of security methods and filters may be applied to fitness goals 54, personal data 56 and other data stored on data storage medium 51 according to a UCID account.

Fitness goals 54 preferably includes data such as target heart rates, target caloric loss, target distance and speed, and other target fitness goals stored in a data storage structure. In addition, fitness goals 54 preferably includes selected exercise programs for particular exercise machines and selected exercise sessions. In particular, an exercise program may be preselected in fitness goals 54 for a particular exercise machine such that the exercise program is automatically selected if a user selects to utilize that particular exercise machine. An exercise program may include a preselected control program from among control programs 58 or may indicate a selection of a predetermined exercise program from among predetermined exercise programs 44. In addition, parameters for the control program, such as a level of difficulty, may also be included in fitness goals 54.

An exercise session may include multiple selections of control programs from among control programs 58 for multiple machines that the user is intended to utilize over a particular period of time. The session of selections of control programs may be pre-selected by the user, determined by a trainer, or selected by remote server system 60 dependent upon the goals of the user and other factors. For example, a session may be selected that includes a control program for a 20-minute interval on a rowing machine at a particular speed and thereafter a control program for a 15-minute interval on a step machine with a target heart rate. Moreover, exercise sessions may include selections of predetermined exercise programs from among predetermined exercise programs 44.

A control program selection or session of control program selections in fitness goals 54 may be added to an electronic calendar 59 on data storage medium 51 in order to schedule for the user what type of exercise should be performed each day and how much time should be allotted for exercise. This function is particularly helpful for users wanting to follow a particular work out schedule. For example, athletes training for an event, such as a triathlon, where a schedule is imperative to reach fitness goals and where multiple diverse exercise modes are performed consecutively, would benefit from an exercise program stored on electronic calendar 59. In addition, a trainer may prescribe a particular workout schedule for a client on electronic calendar 59.

As mentioned previously, if a user or trainer does not select exercise sessions for an individual, remote server system 60 may provide suitable exercise sessions that are selectable by the individual or a trainer utilizing exercise application 50. In particular, exercise application 50 is preferably enabled to determine sessions based on an individual's personal data 56, exercise machines available to the user, and other fitness goals provided such as the type of event training for, the date of the event and other pertinent data. Alternatively, fitness goals may include weight loss, cardiovascular strengthening, muscle strengthening, etc. Preferably, an individual can enter or download specific types of exercise machines that are available in a personal gym or health club utilized by the individual.

Control programs 58 preferably includes multiple control programs for controlling each of multiple types of diverse exercise machines. For example, for a treadmill, one control program may provide for a flat race while another control program may provide for a hill workout. Each of control programs 58 preferably designate a particular type of work out session with goals for reaching particular speeds, heights, heart rates, etc. dependent upon personal data 56. In particular, control programs 56 are preferably downloadable onto data storage medium 51 via remote server system 60.

The parameters of control programs 58 are advantageously adjustable by the user such that the intensity of each control program may be varied. For example, a user may select to utilize a particular control program, such as a hill workout, for thirty minutes one day and for forty-five minutes another day. Remote server system 60 and machine monitor 40 are both preferably enabled to adjust the hill workout control program for varying times, difficulties, etc.

When remote server system 60 is accessed from machine monitor 40, remote server system 60 preferably detects the type of exercise machine from a machine type signal transmitted from exercise machine 38 in the common transmittable data structure format. In response to detecting the type of exercise machine, exercise application 50 executes to check whether a control program or predetermined exercise program for the detected exercise machine is designated in fitness goals 54. If a control program or predetermined exercise program is not preselected, then a selection of control programs is transmitted to machine monitor 40. Machine monitor 40 makes available for selection the control programs and predetermined exercise programs 44. Alternatively, if a control program is preselected, with parameter selections, a machine control signal is transmitted from remote server system 60 to machine monitor 40 in order to control the functions of exercise machine 38. In addition, alternatively, if a predetermined exercise program is selected, the selection is transmitted from remote server system 60 to machine monitor 40 and machine monitor 40 controls the functions of exercise machine 38 according to the predetermined exercise program selection.

As a user exercises, the detected exercise signals received from exercise machine 38 at machine monitor 40 are preferably compared with the goals of the exercise program. Comparison may occur at machine monitor 40 or remote server system 60. For example, a heart rate of the user may be compared with a target heart rate for the control program in view of personal data 56 or a current cumulative fitness activity level in fitness profile 52. If a user is not reaching target goals, an indicator may be output to the user via output interface 45 and/or the machine control signal to exercise machine adjusted to facilitate the user reaching target goals. If the user is exceeding target goals, an indicator may be output to the user via output interface 45 and/or the machine control signal adjusted to reduce exercise intensity.

As another feature of computer system 10, a user may compete against other users via a communications medium with other remote server systems that are monitoring realtime fitness activity data of users according to individual UCID accounts, where the fitness activity data is transmittable in the common data structure format. A user may include a buddy list of UCIDs in personal data 56 such that cumulative fitness activity at each of the buddy UCID accounts is monitored at remote server system 60. In particular, multiple users may be utilizing the same type of exercise machine or diverse types of exercise machines where a single type of display profile or multiple types of display profiles show each of the user's paces compared with the other user's. For example, one user may be riding a stationary bicycle while another user is running on a treadmill. A graphically rendered game may be displayed to each of the user's at each of the user's computer systems that are monitoring their exercise. The game or other application preferably compensates for the differences in types of exercise to show one user's position compared to another user's position in the game. By the present invention, exercisers may compete against other exercisers within a local area or a global area.

As previously described, output preferences may be included with personal data 56 on data storage medium 51 according to a UCID account. The user-designated output preference may designate output preferences for a particular type of output interface 45 for a particular user. Output interface 45 may include, but is not limited to including, a graphical display, an electronic paper, an audio speaker, audio headphones, a tactile detectable device, or a printer. The output preferences may include, but are not limited to specifications such as the size, type and coloring of a font in a graphical display, the type of tactile-detectable output (e.g. Braille), the language or the metric amount displayed.

In addition, the output preferences may designate a particular game or other program that adds a pictorial representation of a fitness profile. For example, a game that displays the user riding through a jungle forest may be selected. Moreover, as will be understood by one with ordinary skill in the art, any output device may perform functions independent of outputting the fitness profile. For example, a user may switch stations, volume and signal bearing media on controllers including, but not limited to, a radio receiver, a television signal receiver, a compact disk player or a tape player that is accessible from exercise machine 38. In addition, as will be understood by one with ordinary skill in the art, any form of visual, auditory or tactile media may be provided for the individual to detect their fitness profile.

Moreover, a user may tender payment to access and/or purchase an exercise game or other media from an alternate UCID account. For example, a UCID account may include multiple graphical exercise games that are designed for use with a particular exercise machine. The user may be provided with a password or other identifier for accessing the exercise game after paying for that password. In another example, a buddy may have a particular exercise game stored according to the buddy's UCID account. A user may access the particular exercise game from the buddy's UCID account by entering the buddy's UCID and a password.

With reference still to FIG. 2, an individual can utilize their UCID account as a personal electronic exercise monitor that accesses, interprets, and manages fitness data across multiple diverse exercise machine platforms. Further, a UCID account may be utilized for varying levels of control of machine monitor 40. For example, for limited control, only the user's personal data may be transmitted from a UCID account to an exercise machine monitor. By transmitting personal data, the user is relieved from re-entering the same personal data across multiple exercise machine monitors. In another example, for another level of control, the user's personal data and an exercise program selection, difficulty and length may be provided to an exercise machine monitor. By transmitting an exercise program selection, difficulty and length, an exercise program from predetermined exercise programs 44 may be selected and adjusted for the user's selected difficulty and length. In another example, for another level of control, a control program may be provided to an exercise machine monitor that controls machine controller 48. Thereby, programming of the machine monitor is completely determined from the UCID account.

It is important to note that a UCID may be entered by a particular user, or alternatively, a UCID may be entered by a particular user on behalf of another user, group of users, or other account holder. In addition, it is important to note that the exercise machine monitoring system of the present invention may provide for a gym setting in which a user's UCID account is charged as the user exercises. For example, a user's UCID account may be debited per machine usage, per type of machine utilized, per time on the machine, per number of calories burned or other criteria. Moreover, a user's account may be debited for downloading a particular game or upgrade.

Figure 3:
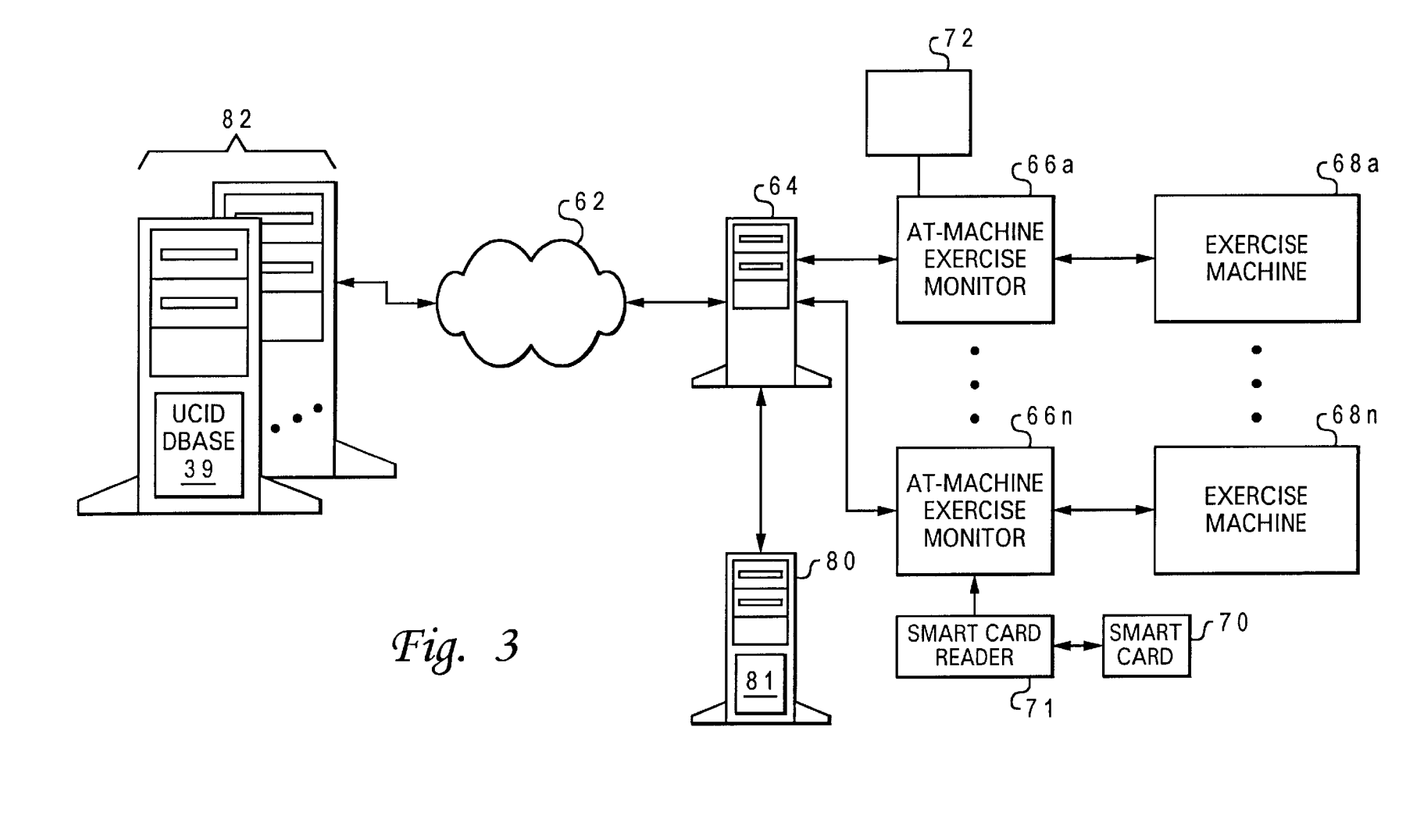
FIG. 3 depicts a pictorial illustration of a network system that provides for data transmission between a universally accessible database and multiple exercise machine monitors in accordance with the method, system and program of the present invention.

Referring now to FIG. 3, there is depicted a pictorial illustration of a network system that provides for data transmission between a universally accessible database of server systems and multiple exercise machine monitors in accordance with the method, system and program of the present invention. Machine monitors 66*a*–66*n* are enabled to retrieve data from and transmit to a universally accessible database of server systems 82 via access to a server system 64 with access to network 62, such as the Internet or other universally accessible network.

Universally accessible database of server systems 82 includes multiple remote server systems. UCID lookup database 37 is preferably included in universally accessible database of server systems 82 and includes a directory of server addresses associated with the UCID accounts that are stored across the multiple remote server systems of universally accessible database of server systems 82.

A UCID and access key may be provided to a machine monitor, such as machine monitor 66n, via a personal storage device. In the example depicted, a smart card reader 71 accesses a smart card 70 that preferably includes a UCID and an access key stored therein. While the example depicted utilizes smart card 70 as a personal storage device, alternate types of personal storage devices which include a UCID and access key may be utilized in the present invention as will be understood by one with ordinary skill in the art. In addition, a user may enter a UCID and key through an alternate peripheral device.

A schedule request for particular exercise machines during a particular time period may be transmitted from universally accessible database of server systems 82 according to a particular UCID account to a health club server 80. Health club server 80 preferably includes a reservation database 81 containing a listing of each exercise machine available and any reservations made for the machines. In addition, time limits for each exercise machine may be specified. The reservation server 80 compares the schedule requests with available time slots in reservation database 81 and transmits a list of available scheduling to a particular UCID account within universally accessible database of server systems 82. An individual with access to the UCID account may then select from the available time slots to reserve exercise machines. In making reservations within reservation database 81, an identifier, such as the UCID associated with the user requesting the reservation, is stored therewith. Preferably, a session of scheduled exercise machines is added to an electronic calendar or other scheduling database included in a UCID account.

Reservation server 80 preferably tracks statistical data concerning the times utilized and frequency of reservation requests for exercise machines. By tracking reservation data, marketing and financial planning data can be collected. For example, peak hours for a health club can be determined. In addition, by tracking reservation data, a member might be limited in the number of times that they can schedule a reservation and later cancel the reservation.

Figure 4:
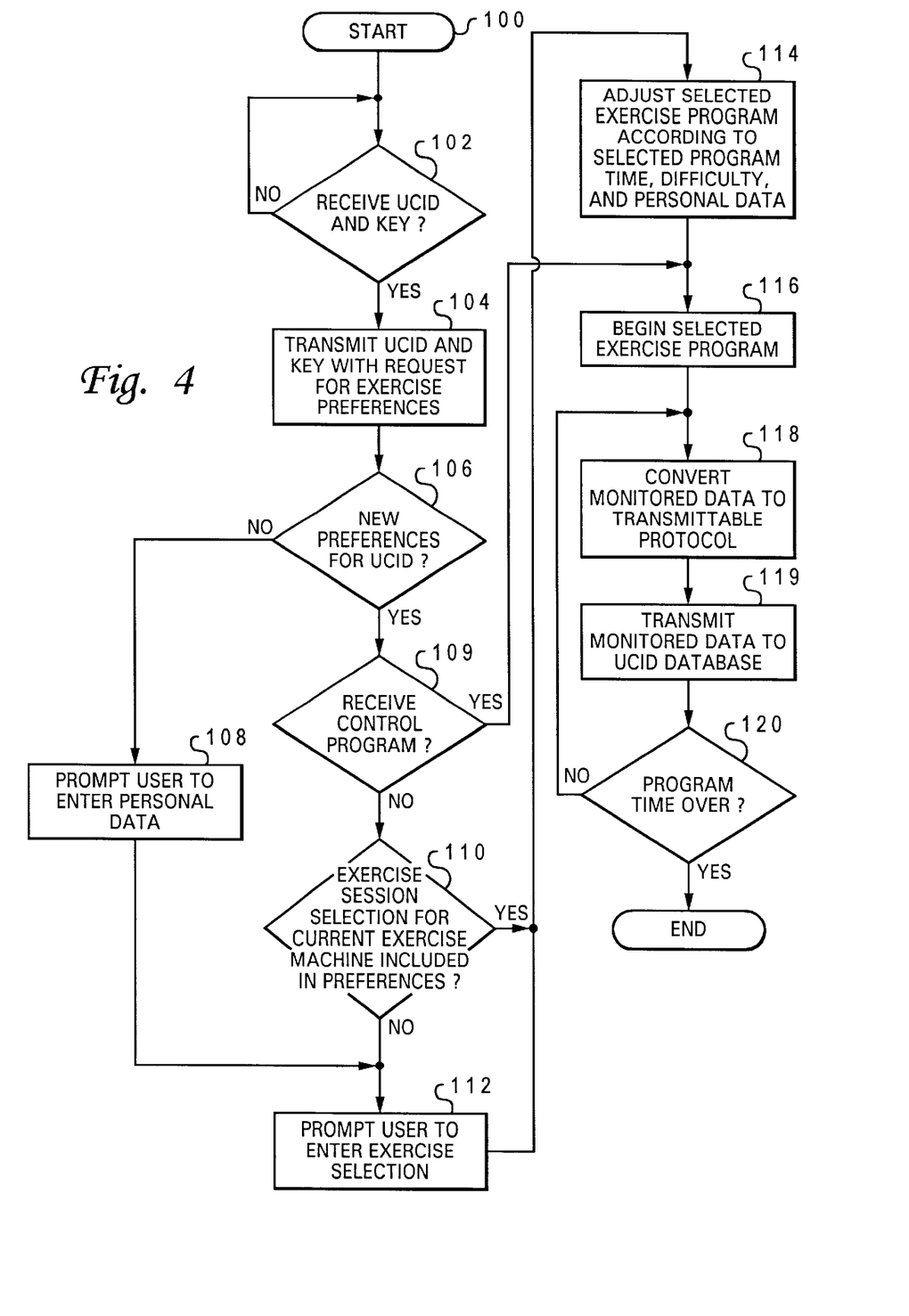
FIG. 4 depicts a high level logic flowchart of a process and program for controlling a machine monitor in accordance with the present invention.

With reference now to FIG. 4, there is illustrated a high level logic flowchart of a process and program for controlling a machine monitor in accordance with the present invention. As depicted, the process starts at block 100 and thereafter proceeds to block 102. Block 102 illustrates a determination as to whether or not a new UCID and key are received. If a new UCID and key are not received, the process iterates at block 102. If a new UCID and key are received, the process passes to block 104. Block 104 depicts transmitting the UCID and key with a request for exercise preferences for the particular type of exercise machine controlled by the machine monitor to the UCID lookup database. Thereafter, block 106 illustrates a determination as to whether or not exercise preferences are received for the UCID from the UCID database. Exercise preferences may include personal data, fitness goals and/or a fitness profile. If exercise preferences are not received, then the process passes to block 108. Block 108 depicts prompting the user for personal data; and the process passes to block 112. If exercise preferences are received, then the process passes to block 109.

Block 109 illustrates a determination as to whether or not a control program is received with the exercise preferences. If a control program is received, then the process passes to block 116. If a control program is not received, the process passes to block 110. Block 110 depicts a determination as to whether or not an exercise program selection, difficulty and time are included with the exercise preferences. If an exercise program selection, difficulty and time are not included in the exercise preferences, then the process passes to block 112. Block 112 illustrates prompting the user to enter and exercise program selection, difficulty and time; and the process passes to block 114. If an exercise program selection, difficulty and time are included in the exercise preferences, then the process passes to block 114.

Block 114 depicts adjusting the selected exercise program according to the selected time difficulty and other personal data. Thereafter, block 116 illustrates beginning the selected exercise program. Next, block 118 depicts updating the UCID account with the monitored data. Thereafter, block 120 illustrates a determination as to whether or not the program time is over. If the program time is not over, then the process passes to block 118. If the program time is over, then the process ends.

Figure 5:
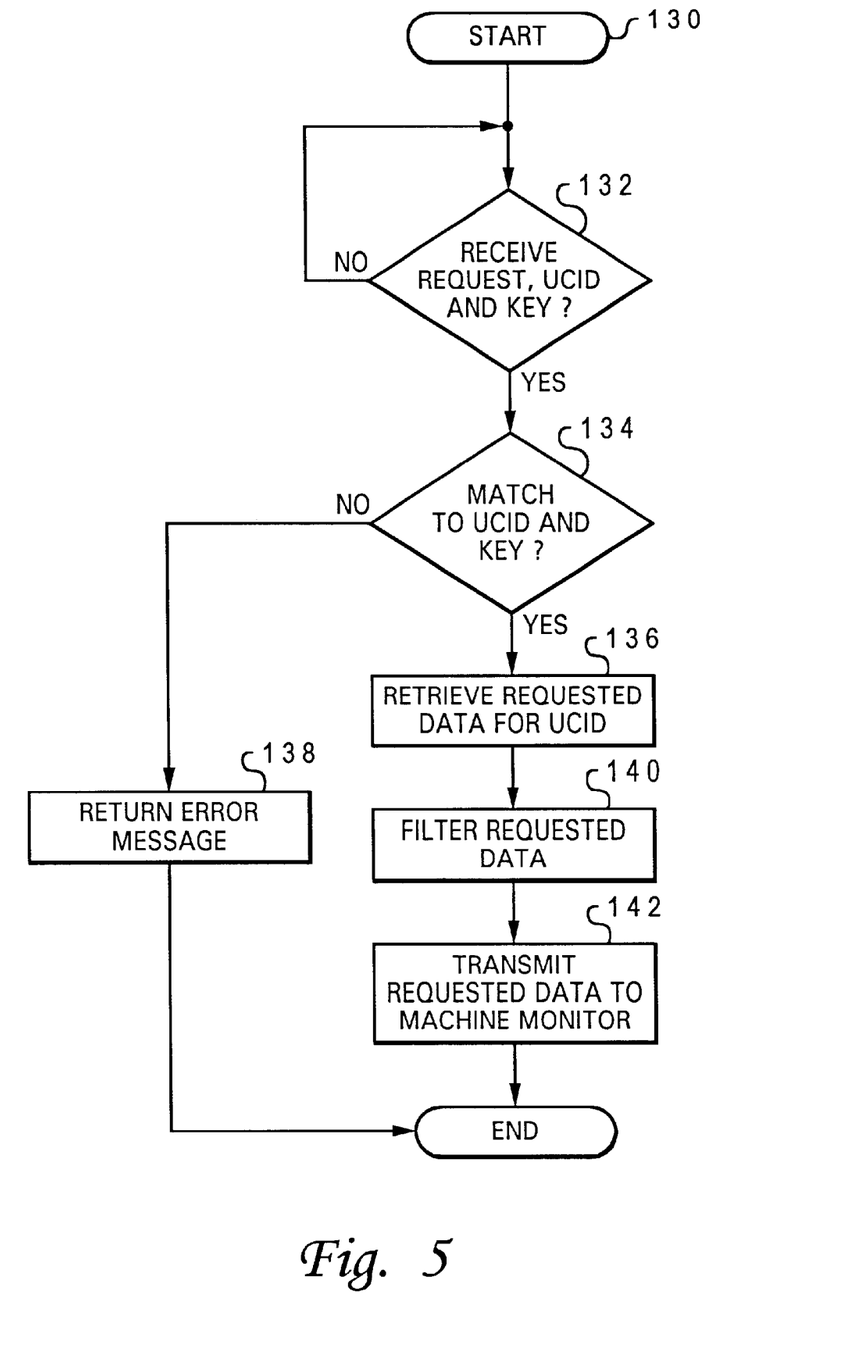
FIG. 5 illustrates a high level logic flowchart of a process and program for utilizing a universally accessible database to control an exercise machine in accordance with the present invention.

Referring now to FIG. 5, there is depicted a high level logic flowchart of a process and program for accessing exercise preferences for a designated UCID account in accordance with the present invention. As illustrated, the process starts at block 130 and thereafter proceeds to block 132. Block 132 depicts a determination as to whether or not a request, UCID and key are received. If a request, UCID and key are not received, then the process iterates at block 132. If a request, UCID and key are received, then the process passes to block 134. Block 134 illustrates a determination as to whether a match to the UCID and key is found in the UCID lookup database. If a match is not found, then the process passes to block 138. Block 138 depicts returning an error message and the process returns. If a match is found, then the process passes to block 136. Block 136 illustrates retrieving the requested data from the UCID account. Thereafter, block 138 depicts filtering the retrieved data with any filtering preferences set within the UCID account. For example, a filtering preference may be set that when a request is made for exercise preferences only age and weight from the personal data of the UCID account are transmittable and not the name, address or telephone number. In addition, in filtering the data, the transmittable data may be encrypted such that only the machine monitor requesting the exercise preferences can decrypt the data. Next, block 142 illustrates transmitting the requested data to the requesting machine monitor; and the process ends.

Figure 6:
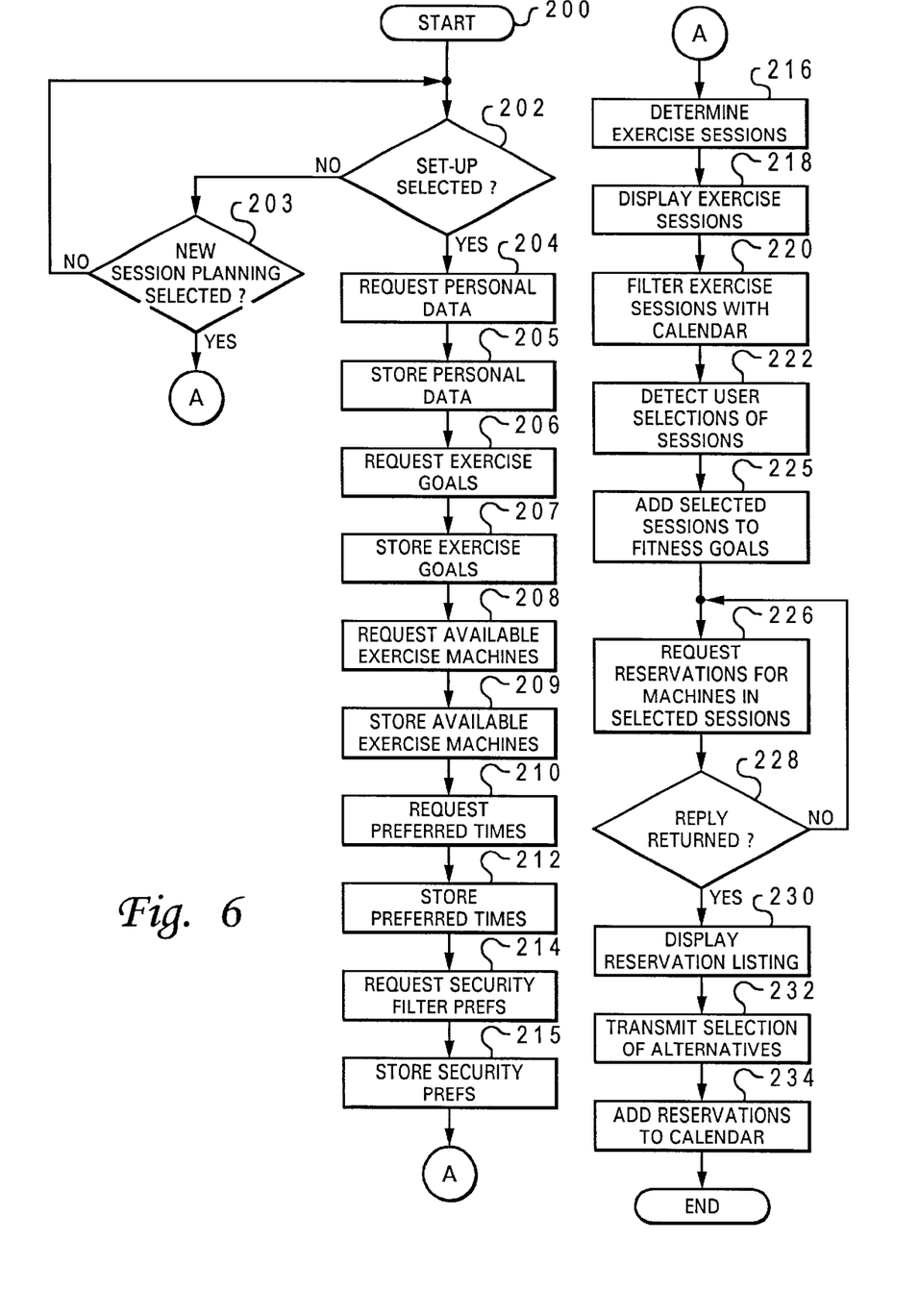
FIG. 6 depicts a high level logic flowchart of a process and program for specializing a exercise data stored in association with an identifier within a universally accessible database in accordance with the present invention.

With reference now to FIG. 6, there is illustrated a high level logic flowchart of a process and program for specializing exercise related data at an identifier associated with a particular user within a universally accessible database in accordance with the method, system and program of the present invention. As depicted, the process starts at block 200 and thereafter proceeds to block 202. Block 202 illustrates a determination as to whether or not a set-up request is made by a user. If a set-up request is made, the process passes to block 204. If a set-up request is not made, the process passes to block 203. Block 203 depicts a determination as to whether or not new session planning is selected. If new session planning is not requested, the process passes to block 202. If new session planning is requested, the process passes to block 216.

Block 204 depicts requesting personal data from the user. Thereafter, block 205 illustrates storing the personal data at the user's identifier. Next, block 206 depicts requesting fitness goals such as race goals, weight loss, cardiovascular strength, etc. Block 207 illustrates storing the fitness goals at the user's identifier. Block 208 depicts requesting a list of exercise machines that are available to the user. The user may download the list of exercise machines, select from a list of pre-loaded exercise machines, or enter new exercise machines. Thereafter, block 209 illustrates storing the available exercise machines at the user's identifier. Next, block 210 depicts requesting 'preferred exercise times. Block 212 illustrates storing the preferred exercise times at the user's identifier. Next, block 214 depicts requesting security filter preferences. Block 215 illustrates storing the security filter preferences with the personal data at the user's identifier. Thereafter, block 216 depicts determining an exercise session or sessions. Next, block 218 illustrates displaying the exercise session or sessions; and the process passes to block 220.

Block 220 illustrates filtering the displayed sessions with the user's calendar stored at the user's identifier; and the process passes to block 222. Block 222 depicts detecting user selections of sessions. In addition to the personal exercise monitor determining suitable exercise sessions, the user may create their own sessions, or sessions may be downloaded from another source. In addition, a session may include control programs for a single exercise machines or for multiple exercise machines. Next, block 225 depicts adding the selected sessions and output preferences to the fitness goals at the user's identifier. Thereafter, block 226 illustrates transmitting a request for reservations for the exercise machines included in the selected sessions. Next, block 228 depicts a determination as to whether or not a reply is received from a reservation server. If a reply is not received, the process passes to block 226. If a reply is received, the process passes to block 230. Block 230 illustrates displaying the reservation listing. Preferably the reservation listing includes exercise machines that have confirmed reservations and alternatives for unavailable machine requests. Block 232 depicts transmitting selections from alternatives. Block 234 illustrates adding the reservations to the user's electronic calendar stored at the user's identifier; and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for monitoring the fitness activity of an exerciser, said method comprising the steps of:

receiving at least one type of exercise indicator signal associated with exercise performed by a particular user from a particular exercise machine in a particular mark-up language format at a universally accessible server system in accordance with a universal identifier associated with said particular user, and storing said at least one type of exercise indicator signal as current fitness activity for said particular user at said universally accessible server system wherein said at least one type of exercise indicator signal is stored in association with said universal identifier to identify said current fitness activity for said particular user, such that a universally accessible server system in accordance with a universal identifier associated with said particular user monitors the real-time fitness activity of said particular user from said at least one type of exercise indicator signal received from at least one exercise machine.

2. The method for monitoring the fitness activity of an exerciser according to claim 1, said step of receiving at least one type of exercise indicator signal associated with exercise performed by said particular user from a particular exercise machine from among a plurality of accessible exercise machines in a particular transmittable data format, further comprising the step of:

receiving said at least one type of exercise indicator signal in an extensible mark-up language format.

3. The method for monitoring fitness activity from an exercise machine according to claim 1, said method further comprising the step of:

computing said current fitness activity according to said at least one type of exercise indicator signal and a profile of said particular user at said universally accessible server system in accordance with said universal identifier.

4. The method for monitoring fitness activity from an exercise machine according to claim 1, said method further comprising the step of:

computing cumulative fitness activity for said particular user at said universally accessible server system from said current fitness activity and from previously computed fitness activity for said particular user computed and stored during a particular period of time as a result of exercise at any of said plurality of diverse exercise machines.

5. The method for monitoring fitness activity from an exercise machine according to claim 1, said method further comprising the step of:

transmitting a control signal from said universally accessible server system in accordance with said universal identifier to said particular exercise machine in said common transmittable data format for temporarily controlling said particular exercise machine while in use by said particular user.

6. The method for monitoring fitness activity from an exercise machine according to claim 1, said method further comprising the step of:

transmitting personal data and a program selection for said particular user from said universally accessible server system in accordance with said universal identifier to said particular exercise machine in said common transmittable data format, in order to initialize an at-machine monitor for use by said particular user.

7. The method for monitoring fitness activity from an exercise machine according to claim 6, said method further comprising the steps of:

receiving a machine type indicator from said particular exercise machine at said universally accessible server system in accordance with said universal identifier;

searching a plurality of designated program selections according to said machine type indicator; and transmitting a particular program selection from among said plurality of designated program selections, wherein said particular program selection is designated for automatic transmission to said particular exercise machine when said machine type indicator for said particular exercise machine is received.

8. The method for monitoring fitness activity from an exercise machine according to claim 6, said method further comprising the steps of:
    detecting an exercise event for said particular user for said particular exercise machine in an electronic schedule at said universally accessible server system in accordance with said universal identifier; and
    transmitting said program selection according to said exercise event.

9. The method for monitoring fitness activity from an exercise machine according to claim 1, said method further comprising the step of:
    accessing a graphical output application from said universally accessible server system in accordance with said universal identifier at said particular exercise machine monitor, wherein output from said particular exercise machine monitor is controlled according to said graphical output application.

10. The method for monitoring fitness activity from an exercise machine according to claim 1, said method further comprising the step of:
    accessing a graphical output application from an alternate universally accessible server system in accordance with an alternate universal identifier to said particular exercise machine monitor, wherein output from said particular exercise machine monitor is controlled according to said graphical output application.

11. The method for monitoring fitness activity from an exercise machine according to claim 1, said method further comprising the step of:
    allowing access to said stored current fitness activity for said particular user by an alternate user via said universally accessible server system in accordance with said universal identifier.

12. The method for monitoring fitness activity from an exercise machine according to claim 1, said method further comprising the step of:
    receiving payment for any access to said current fitness activity for said particular user via said universally accessible server system in accordance with said universal identifier by said alternate user.

13. The method for monitoring fitness activity from an exercise machine according to claim 1, said method further comprising the step of:
    accessing stored current fitness activity of an alternate user from an alternate universally accessible server system according to an alternate universal identifier associated with said alternate user at said particular exercise machine in use by said particular user.

14. The method for monitoring fitness activity from an exercise machine according to claim 1, said method further comprising the steps of:
    transmitting a request for a reservation for a particular exercise machine for a particular time period from said universally accessible server system in accordance with said universal identifier to a reservation server for a plurality of exercise machines; and
    adding an exercise event for said reservation to an electronic schedule at said universally accessible server system in accordance with said universal identifier, in response to receiving a reservation verification at said universally accessible server system in accordance with said universal identifier.

15. The method for monitoring fitness activity from an exercise machine according to claim 1, said method further comprising the step of:
    debiting an account at said universally accessible server system in accordance with said universal identifier according to usage of said particular exercise machine.

16. The method for monitoring fitness activity from an exercise machine according to claim 1, said method further comprising the step of:
    accessing a description of each of a plurality of exercise machines that are accessible to said user at said universally accessible server system according to said universal identifier.

17. A system for monitoring the fitness activity of an exerciser, said system comprising:
    means for receiving at least one type of exercise indicator signal associated with exercise performed by a particular user from a particular exercise machine from among a plurality of accessible exercise machines in a particular mark-up language format at a universally accessible server system in accordance with a universal identifier associated with said particular user; and
    means for storing said at least one type of exercise indicator signal as current fitness activity for said particular user at said universally accessible server system wherein said at least one type of exercise indicator signal is stored in association with said universal identifier to identify said current fitness activity for said particular user, such that a universally accessible server system in accordance with a universal identifier associated with said particular user monitors the real-time fitness activity of said particular user from said at least one type of exercise indicator signal received from at least one exercise machine.

18. The system for monitoring the fitness activity of an exerciser according to claim 17, said means for receiving at least one type of exercise indicator signal associated with exercise performed by said particular user from a particular exercise machine from among a plurality of accessible exercise machines in a particular transmittable data format, further comprising:
    means for receiving said at least one type of exercise indicator signal in an extensible mark-up language format.

19. The system for monitoring fitness activity from an exercise machine according to claim 17, said system further comprising:
    means for computing said current fitness activity according to said at least one type of exercise indicator signal and a profile of said particular user at said universally accessible server system in accordance with said universal identifier.

20. The system for monitoring fitness activity from an exercise machine according to claim 17, said system further comprising:
    means for computing cumulative fitness activity for said particular user at said universally accessible server system from said current fitness activity and from previously computed fitness activity for said particular user computed and stored during a particular period of time as a result of exercise at any of said plurality of diverse exercise machines.

21. The system for monitoring fitness activity from an exercise machine according to claim 17, said system further comprising:
    means for transmitting a control signal from said universally accessible server system in accordance with said universal identifier to said particular exercise machine in said common transmittable data format for temporarily controlling said particular exercise machine while in use by said particular user.

22. The system for monitoring fitness activity from an exercise machine according to claim 17, said system further comprising:

means for transmitting personal data and a program selection for said particular user from said universally accessible server system in accordance with said universal identifier to said particular exercise machine in said common transmittable data format, in order to initialize an at-machine monitor for use by said particular user.

23. The system for monitoring fitness activity from an exercise machine according to claim 22, said system further comprising:

means for receiving a machine type indicator from said particular exercise machine at said universally accessible server system in accordance with said universal identifier;

means for searching a plurality of designated program selections according to said machine type indicator; and means for transmitting a particular program selection from among said plurality of designated program selections, wherein said particular program selection is designated for automatic transmission to said particular exercise machine when said machine type indicator for said particular exercise machine is received.

24. The system for monitoring fitness activity from an exercise machine according to claim 22, said system further comprising:

means for detecting an exercise event for said particular user for said particular exercise machine in an electronic schedule at said universally accessible server system in accordance with said universal identifier; and means for transmitting said program selection according to said exercise event.

25. The system for monitoring fitness activity from an exercise machine according to claim 17, said system further comprising:

means for accessing a graphical output application from said universally accessible server system in accordance with said universal identifier at said particular exercise machine monitor, wherein output from said particular exercise machine monitor is controlled according to said graphical output application.

26. The system for monitoring fitness activity from an exercise machine according to claim 17, said system further comprising:

means for accessing a graphical output application from an alternate universally accessible server system in accordance with an alternate universal identifier to said particular exercise machine monitor, wherein output from said particular exercise machine monitor is controlled according to said graphical output application.

27. The system for monitoring fitness activity from an exercise machine according to claim 17, said system further comprising:

means for accessing a description of each of a plurality of exercise machines that are accessible to said user at said universally accessible server system according to said universal identifier.

28. The system for monitoring fitness activity from an exercise machine according to claim 17, said system further comprising:

means for allowing access to said stored current fitness activity for said particular user by an alternate user via said universally accessible server system in accordance with said universal identifier.

29. The system for monitoring fitness activity from an exercise machine according to claim 17, said system further comprising:

means for receiving payment for any access to said current fitness activity for said particular user via said universally accessible server system in accordance with said universal identifier by said alternate user.

30. The system for monitoring fitness activity from an exercise machine according to claim 17, said system further comprising:

means for accessing stored current fitness activity of an alternate user from an alternate universally accessible server system according to an alternate universal identifier associated with said alternate user at said particular exercise machine in use by said particular user.

31. The system for monitoring fitness activity from an exercise machine according to claim 17, said system further comprising:

means for transmitting a request for a reservation for a particular exercise machine for a particular time period from said universally accessible server system in accordance with said universal identifier to a reservation server for a plurality of exercise machines; and means for adding an exercise event for said reservation to an electronic schedule at said universally accessible server system in accordance with said universal identifier, in response to receiving a reservation verification at said universally accessible server system in accordance with said universal identifier.

32. The system for monitoring fitness activity from an exercise machine according to claim 17, said system further comprising:

means for debiting an account at said universally accessible server system in accordance with said universal identifier according to usage of said particular exercise machine.

33. A program for monitoring the fitness activity of an exerciser, said program comprising:

means for receiving at least one type of exercise indicator signal associated with exercise performed by a particular user from a particular exercise machine from among a plurality of accessible exercise machines in a particular mark-up language format at a universally accessible server system in accordance with a universal identifier associated with said particular user; and means for storing said at least one type of exercise indicator signal as current fitness activity for said particular user at said universally accessible server system wherein said at least one type of exercise indicator signal is stored in association with said universal identifier to identify said current fitness activity for said particular user, such that a universally accessible server system in accordance with a universal identifier associated with said particular user monitors the real-time fitness activity of said particular user from said at least one type of exercise indicator signal received from at least one exercise machine.

34. The program for monitoring the fitness activity of an exerciser according to claim 33, said program further comprising:

means for receiving said at least one type of exercise indicator signal in an extensible mark-up language format.

35. The program for monitoring fitness activity from an exercise machine according to claim 33, said program further comprising:

means for computing said current fitness activity according to said at least one type of exercise indicator signal and a profile of said particular user at said universally accessible server system in accordance with said universal identifier.

36. The program for monitoring fitness activity from an exercise machine according to claim 33, said program further comprising:

means for computing cumulative fitness activity for said particular user at said universally accessible server system from said current fitness activity and from previously computed fitness activity for said particular user computed and stored during a particular period of time as a result of exercise at any of said plurality of diverse exercise machines.

37. The program for monitoring fitness activity from an exercise machine according to claim 33, said program further comprising:

means for transmitting a control signal from said universally accessible server system in accordance with said universal identifier to said particular exercise machine in said common transmittable data format for temporarily controlling said particular exercise machine while in use by said particular user.

38. The program for monitoring fitness activity from an exercise machine according to claim 33, said program further comprising:

means for transmitting personal data and a program selection for said particular user from said universally accessible server system in accordance with said universal identifier to said particular exercise machine in said common transmittable data format, in order to initialize an at-machine monitor for use by said particular user.

39. The program for monitoring fitness activity from an exercise machine according to claim 38, said program further comprising:

means for receiving a machine type indicator from said particular exercise machine at said universally accessible server system in accordance with said universal identifier;

means for searching a plurality of designated program selections according to said machine type indicator; and means for transmitting a particular program selection from among said plurality of designated program selections, wherein said particular program selection is designated for automatic transmission to said particular exercise machine when said machine type indicator for said particular exercise machine is received.

40. The program for monitoring fitness activity from an exercise machine according to claim 38, said program further comprising:

means for detecting an exercise event for said particular user for said particular exercise machine in an electronic schedule at said universally accessible server system in accordance with said universal identifier; and means for transmitting said program selection according to said exercise event.

41. The program for monitoring fitness activity from an exercise machine according to claim 33, said program further comprising:

means for accessing a graphical output application from said universally accessible server system in accordance with said universal identifier at said particular exercise machine monitor, wherein output from said particular exercise machine monitor is controlled according to said graphical output application.

42. The program for monitoring fitness activity from an exercise machine according to claim 33, said program further comprising:

means for accessing a graphical output application from an alternate universally accessible server system in accordance with an alternate universal identifier to said particular exercise machine monitor, wherein output from said particular exercise machine monitor is controlled according to said graphical output application.

43. The program for monitoring fitness activity from an exercise machine according to claim 33, said program further comprising:

means for accessing a description of each of a plurality of exercise machines that are accessible to said user at said universally accessible server system according to said universal identifier.

44. The program for monitoring fitness activity from an exercise machine according to claim 33, said program further comprising:

means for allowing access to said stored current fitness activity for said particular user by an alternate user via said universally accessible server system in accordance with said universal identifier.

45. The program for monitoring fitness activity from an exercise machine according to claim 33, said program further comprising:

means for receiving payment for any access to said current fitness activity for said particular user via said universally accessible server system in accordance with said universal identifier by said alternate user.

46. The program for monitoring fitness activity from an exercise machine according to claim 33, said program further comprising:

means for accessing stored current fitness activity of an alternate user from an alternate universally accessible server system according to an alternate universal identifier associated with said alternate user at said particular exercise machine in use by said particular user.

47. The program for monitoring fitness activity from an exercise machine according to claim 33, said program further comprising:

means for transmitting a request for a reservation for a particular exercise machine for a particular time period from said universally accessible server system in accordance with said universal identifier to a reservation server for a plurality of exercise machines; and means for adding an exercise event for said reservation to an electronic schedule at said universally accessible server system in accordance with said universal identifier, in response to receiving a reservation verification at said universally accessible server system in accordance with said universal identifier.

48. The program for monitoring fitness activity from an exercise machine according to claim 33, said program further comprising:

means for debiting an account at said universally accessible server system in accordance with said universal identifier according to usage of said particular exercise machine.

49. A method for competing against a plurality of exercisers, said method comprising the steps of:

receiving current fitness activity for a first exerciser exercising on a first exercise machine in a particular mark-up language format at an exercise machine monitor for monitoring exercise performed by a second exerciser on a second exercise machine, wherein said current fitness activity is received at said exercise machine monitor from a universally accessible server system, wherein said current fitness activity for a first exerciser is identified by a universal identifier associated with said first exerciser; and displaying a graphical comparison of said current fitness activity for said first exerciser with current fitness activity for said second exerciser from an output interface controlled by said exercise machine monitor, such that said second exerciser is enabled compete against a plurality of exercisers.

50. The method for competing against a plurality of exercisers according to claim 49, said method further comprising the step of:

accessing current fitness activity data for a plurality of exercisers at said exercise machine monitor from a universally accessible server system in accordance with a universal identifier associated with a group comprising said plurality of exercisers.

51. The method for competing against a plurality of exercisers according to claim 49, said method further comprising the step of:

receiving a graphical output application for displaying a graphical comparison of said current fitness activity from an alternate universally accessible server system in accordance with an alternate universal identifier associated with an application provider.

52. The method for competing against a plurality of exercisers according to claim 49, said step of displaying a graphical comparison of said current fitness activity for said first exerciser with current fitness activity for said second exerciser further comprising the step of:

displaying a graphical comparison of said current fitness activity for said first exerciser from exercise performed on a first type of exercise machine with a with said current fitness activity for said second exerciser from exercise performed on a second type of exercise machine.

53. A system for competing against a plurality of exercisers, said system comprising:

means for receiving current fitness activity for a first exerciser exercising on a first exercise machine in a particular mark-up language format at an exercise machine monitor for monitoring exercise performed by a second exerciser on a second exercise machine, wherein said current fitness activity is received at said exercise machine monitor from a universally accessible server system, wherein said current fitness activity for a first exerciser is identified by a universal identifier associated with said first exerciser; and means for displaying a graphical comparison of said current fitness activity for said first exerciser with current fitness activity for said second exerciser from an output interface controlled by said exercise machine monitor, such that said second exerciser is enabled compete against a plurality of exercisers.

54. The system for competing against a plurality of exercisers according to claim 53, said system further comprising:

means for receiving a graphical output application for displaying a graphical comparison of said current fitness activity from an alternate universally accessible server system in accordance with an alternate universal identifier associated with an application provider.

55. The system for competing against a plurality of exercisers according to claim 53, said means for displaying a graphical comparison of said current fitness activity for said first exerciser with current fitness activity for said second exerciser further comprising:

means for displaying a graphical comparison of said current fitness activity for said first exerciser from exercise performed on a first type of exercise machine with said current fitness activity for said second exerciser from exercise performed on a second type of exercise machine.

56. A universally accessible database of server systems comprising:

a plurality of universally accessible server systems each with access respectively to one of a plurality of data storage mediums, wherein a particular data storage medium comprises current fitness activity stored in a mark-up language format for a particular user according to a particular universal identifier; and a communication interface between said plurality of universally accessible server systems and a controller for an exercise machine from among a plurality of exercise machines for receiving current fitness activity of said particular user on said exercise machine at said particular data storage medium.

57. The universally accessible database of server systems according to claim 56, said system further comprising:

an account server system comprising a lookup database of a plurality of universal identifiers, wherein said plurality of universally accessible server systems are accessible as each respectively associated with said plurality of universal identifiers.

58. The universally accessible database of server systems according to claim 56, wherein said particular data storage medium further comprises an electronic schedule for a particular user comprising a plurality of scheduled exercise events utilizing a plurality of exercise machines.

59. The universally accessible database of server systems according to claim 56, wherein said particular data storage medium further comprises a plurality of control programs each respectively designated for controlling one of a plurality of exercise machines when accessed via said interface at one of said plurality of exercise machines.

60. The universally accessible database of server systems according to claim 56, wherein said particular data storage medium further comprises a user profile for said particular user that when accessed via said interface at said controller for said exercise machine initializes said controller.

* * * * *